(12) United States Patent
Abrams

(10) Patent No.: US 8,686,027 B1
(45) Date of Patent: Apr. 1, 2014

(54) METHOD FOR TREATING BRONCHIAL DISEASES

(75) Inventor: Andrew Abrams, Westport, CT (US)

(73) Assignee: Microdose Therapeutx, Inc., Monmouth Junction, NJ (US)

( * ) Notice: Subject to any disclaimer, the term of this patent is extended or adjusted under 35 U.S.C. 154(b) by 197 days.

(21) Appl. No.: 13/313,936

(22) Filed: Dec. 7, 2011

Related U.S. Application Data

(62) Division of application No. 10/372,487, filed on Feb. 21, 2003, now Pat. No. 8,168,674.

(60) Provisional application No. 60/359,218, filed on Feb. 22, 2002.

(51) Int. Cl.
| | |
|---|---|
| *A01N 43/36* | (2006.01) |
| *A61K 31/40* | (2006.01) |
| *A01N 43/08* | (2006.01) |
| *A61K 31/34* | (2006.01) |
| *A61K 9/14* | (2006.01) |

(52) U.S. Cl.
USPC .......................... 514/428; 514/471; 424/489

(58) Field of Classification Search
USPC ................... 514/428, 471; 424/489
See application file for complete search history.

(56) References Cited

U.S. PATENT DOCUMENTS

| | | | |
|---|---|---|---|
| 4,908,382 A | 3/1990 | Bianco | 514/471 |
| 5,182,300 A | 1/1993 | Pellegata | 514/471 |
| 5,392,767 A | 2/1995 | Bianco | 128/200.14 |
| 5,739,361 A | 4/1998 | Signor et al. | 549/494 |
| 6,026,809 A | 2/2000 | Abrams et al. | 128/203.15 |

FOREIGN PATENT DOCUMENTS

| | | | | |
|---|---|---|---|---|
| DE | 4123914 | 1/1993 | | A61K 31/44 |

OTHER PUBLICATIONS

"Expert Opinion on Investigational Drugs" by Godfried M. Roomans 2001 pp. 1-19 (19pgs).

*Primary Examiner* — Yong Chong
(74) *Attorney, Agent, or Firm* — Hayes Soloway P.C.

(57) ABSTRACT

Administration of a loop diuretic in nebulized dry powder form directly to a patient's lungs for treating bronchial disease.

6 Claims, No Drawings

METHOD FOR TREATING BRONCHIAL DISEASES

CROSS-REFERENCE TO RELATED APPLICATIONS

This application is a divisional of U.S. application Ser. No. 10/372,487, filed Feb. 21, 2003, now U.S. Pat. No. 8,168,674, issued May 1, 2012, which in turn claims benefit from U.S. Provisional Patent Application Ser. No. 60/359,218, filed Feb. 22, 2002.

FIELD OF THE INVENTION

The present invention relates to treatment of patients to provide bronchial relief.

BACKGROUND OF THE INVENTION

Bronchial diseases such as asthma, emphysema, cystic fibrosis, dyspnea, chronic bronchitis, and chronic obstructive pulmonary disease (COPD), is a major health problem affecting millions of people worldwide. The magnitude of bronchial diseases has placed emphasis on the need to develop new treatment strategies.

Currently, the conventional treatment of asthma and other bronchitis diseases involves the use of steroids such as prednisone, which is administered orally, and other steroids and beta adrenergics such as albuterol, which are administered via an inhaler. However, such treatments have significant adverse side affects.

It is therefore an object of the invention to provide an alternative treatment for bronchial diseases that does not suffer from the usual adverse side affects of conventional treatments.

BRIEF DESCRIPTION OF THE INVENTION

I have found that loop diuretics such as Furosemide (4-chloro-N-(2-furylmethyl)-5-sulfamoyl anthranilic acid) or ethacrynic acid when administered in nebulized dry powder form directly to a patient's lungs advantageously may be used for treating bronchial disease.

DETAILED DESCRIPTION OF PREFERRED EMBODIMENT

Furosemide is a well-known diuretic agent of the formula I and its effects have been studied extensively. The drug usually is given orally, i.e., in table form, but can be administered in solution intravenously to promote diuresis.

U.S. Pat. No. 4,908,382 to Bianco describes the administration by inhalation in a solution in water of Furosemide, i.e., by means of a nebulizer, advantageously may be employed in preventing exercise-induced broncho-constriction.

In the present invention, nebulized dry powder loop diuretic such as Furosemide or ethacrynic acid is used to relieve bronchial constriction. Delivery of a loop diuretic in dry powder form is advantageous in that it permits delivery of the drug conveniently and optimally into the lungs.

Loop diuretics such as ethacrynic acid and Furosemide are available commercially from a variety of manufacturers in both tablet and solution form. Alternatively, Furosemide may be produced following the teachings of U.S. Pat. No. 5,739,361 to Signor et al., which patent is incorporated herein by reference. For optimal delivery to the lungs, dry powder form of the loop diuretic should be micronized or spray dried to a powder size of 0.5-10 microns, preferably 1-6 microns.

The dry powder loop diuretic may then be put into a conventional dry powder inhaler (DPI) in a systemically effective unit dose delivery amount between about 1 and 100 milligrams of the loop diuretic, as needed, typically 1 to 4 times per day.

The dry powder delivery of a loop diuretic to the respiratory tract can be used advantageously to treat asthma, emphysema, cystic fibrosis, dyspnea, chronic bronchitis, and chronic obstructive pulmonary disease (COPD). Unexpectedly, administration of dry powder Furosemide directly to the lungs does not produce diuresis.

The following examples are provided to further illustrate the present invention.

Example 1

Furosemide in crystalline form is prepared following Example 3 of the U.S. Pat. No. 5,739,361. The resulting crystalline powder is micronized to a maximum particle size of about 10 microns. The powder is packaged for unit dose delivery of 10 milligrams in a dry powder inhaler (DPI) made in accordance with my earlier U.S. Pat. No. 6,026,809.

Example 2

Furosemide was prepared as in Example 1, and packaged for delivery in a DPI as before for delivery of 5 milligrams per dose.

Delivery of 5-40 milligrams of Furosemide delivered as needed was found to provide relief to patients suffering from asthma, emphysema, cystic fibrosis, chronic bronchitis, COPD and dyspnea.

While the invention has been described in detail herein in accordance with certain preferred embodiments thereof, many modifications and changes therein may be affected by those skilled in the art. Accordingly, it is intended that the pended claims cover all such modifications and changes as may fall within the spirit and scope of the invention.

The invention claimed is:

1. A method for relieving a symptom of pulmonary disease in a patient suffering therefrom, wherein the pulmonary disease is selected from the group consisting of emphysema, cystic fibrosis, chronic bronchitis, chronic obstructive pulmonary disease (COPD) and dyspnea, comprising delivering directly to the patient's lungs a systemically effective amount of a non-salt formulation of furosemide and ethacrynic acid in dry powder form, wherein said systematically effective amount of a non-salt formulation is delivered as a fine powder having a particle size of 0.5-10 microns.

2. The method accordingly to claim 1, wherein said systematically effective amount of a non-salt formulation is delivered in unit dose amounts of between about 1 and 100 milligrams.

3. The method according to claim 2, wherein said systematically effective amount of a non-salt formulation is delivered in unit dose amounts of between about 5 and 10 milligrams.

4. The method according to claim 1, wherein said systematically effective amount of a non-salt formulation is delivered in discrete doses as needed.

5. The method according to claim 4, wherein said systematically effective amount of a non-salt formulation is delivered in discrete doses 1-4 times per day.

6. The method according to claim 1, wherein said systematically effective amount of a non-salt formulation is delivered in dry powder form having a powder size of 1-6 microns.

\* \* \* \* \*

UNITED STATES PATENT AND TRADEMARK OFFICE
CERTIFICATE OF CORRECTION

PATENT NO.        : 8,686,027 B1
APPLICATION NO.   : 13/313936
DATED             : April 1, 2014
INVENTOR(S)       : Andrew Abrams Page 1 of 1

It is certified that error appears in the above-identified patent and that said Letters Patent is hereby corrected as shown below:

In the Claims:

Claim 1, Col. 2, lines 56-58, "selected from the group consisting of emphysema, cystic fibrosis, chronic bronchitis, chronic obstructive pulmonary disease (COPD) and dyspnea" should be --chronic obstructive pulmonary disease (COPD)--.

Signed and Sealed this
Thirtieth Day of September, 2014

Michelle K. Lee
*Deputy Director of the United States Patent and Trademark Office*